(12) United States Patent
Akahoshi

(10) Patent No.: US 8,876,750 B2
(45) Date of Patent: Nov. 4, 2014

(54) COAXIAL TUBING SYSTEM FOR PHACOEMULSIFICATION HANDPIECES

(75) Inventor: Takayuki Akahoshi, Tokyo (JP)

(73) Assignee: Art, Limited, Grand Cayman (KY)

( * ) Notice: Subject to any disclaimer, the term of this patent is extended or adjusted under 35 U.S.C. 154(b) by 436 days.

(21) Appl. No.: 11/069,773

(22) Filed: Mar. 1, 2005

(65) Prior Publication Data

US 2006/0079832 A1   Apr. 13, 2006

Related U.S. Application Data

(60) Provisional application No. 60/613,645, filed on Sep. 27, 2004.

(51) Int. Cl.
  *A61M 1/00* (2006.01)
  *A61M 3/00* (2006.01)
  *A61F 9/007* (2006.01)

(52) U.S. Cl.
  CPC .......... *A61M 1/0084* (2013.01); *A61F 9/00745* (2013.01); *A61M 2210/0612* (2013.01); *A61M 1/0064* (2013.01)
  USPC ............................................. 604/27; 604/43

(58) Field of Classification Search
  USPC .............. 604/27, 22, 30, 28, 43, 275, 31, 35, 604/272; 606/167, 107, 170, 180, 27, 46; 433/81
  See application file for complete search history.

(56) References Cited

U.S. PATENT DOCUMENTS

| | | | | |
|---|---|---|---|---|
| 4,515,583 A | * | 5/1985 | Sorich | 604/22 |
| 4,808,155 A | * | 2/1989 | Mahurkar | 604/43 |
| 5,364,405 A | * | 11/1994 | Zaleski | 606/107 |
| 5,403,317 A | * | 4/1995 | Bonutti | 606/80 |
| 5,405,321 A | * | 4/1995 | Reeves | 604/44 |
| 5,830,176 A | * | 11/1998 | Mackool | 604/22 |
| 5,980,529 A | * | 11/1999 | Strukel | 606/107 |
| 5,989,209 A | * | 11/1999 | Barrett | 604/22 |
| 6,589,201 B1 | * | 7/2003 | Sussman et al. | 604/27 |
| 6,607,503 B1 | * | 8/2003 | Berbers | 604/27 |
| 2002/0183731 A1 | * | 12/2002 | Holland et al. | 606/21 |
| 2003/0040763 A1 | * | 2/2003 | Moutafis et al. | 606/167 |
| 2004/0092791 A1 | * | 5/2004 | Bateman et al. | 600/34 |

* cited by examiner

*Primary Examiner* — Jason Flick
(74) *Attorney, Agent, or Firm* — Wood, Phillips, Katz, Clark & Mortimer

(57) ABSTRACT

An irrigation and aspiration tubing system for use with surgical handpieces and irrigation fluid supplies has a first flexible irrigation tube for transporting irrigation fluid to the handpiece and a second flexible aspiration tube disposed within the first tube. The inner diameter of the first tube is selected to provide a cross-sectional area available for fluid flow in excess of the cross-sectional area of a standard surgical irrigation tubes. The system also includes at least one adaptor to allow the tubing to be attached to known surgical handpieces. Preferably, a second adaptor is also provided allowing attachment to sources of irrigating fluid and aspiration vacuum. The system finds particular utility with phacoemulsification instruments used for opthhalmic surgery.

11 Claims, 4 Drawing Sheets

US 8,876,750 B2

COAXIAL TUBING SYSTEM FOR PHACOEMULSIFICATION HANDPIECES

This invention relates to surgical instruments and surgical techniques used in eye surgery and more particularly, to phacoemulsification apparatus and methods for their use. This application claims priority from provisional application Ser. No. 60/613,645, filed Sep. 27, 2004.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through a relatively small incision, allowing the lens to unfold when it is properly positioned within the capsular bag. Techniques and instruments have also been developed to accomplish the removal of the diseased lens through an equally small incision.

One such technique is known as phacoemulsification. A typical phacoemulsification system includes a handpiece having a tip sized to fit through a small incision. Within the tip a hollow needle is vibrated at ultrasonic frequencies in order to fragment the diseased lens into small enough particles to be aspirated from the eye. Commonly, an irrigation sleeve is mounted around the needle through which irrigating liquids are infused into the eye to flush the lens particles created by the vibrations. Often the needle is hollow and forms a pathway to aspirate the irrigating fluid and lens particles from the eye. In this way both aspiration and irrigation are performed by a single instrument requiring only a single incision.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small an incision as possible during such surgery is to minimization any leakage of liquid during and after surgery to prevent tissue collapse.

Separate flow paths are required for the infusing and aspirating functions to be carried out properly. This requires the use of separate lengths of flexible tubing extending from the handpiece to the flow system control module. Typically these tubing lengths are on the order of 200 to 250 cm. Because the aspiration and irrigation tubes both go from the handpiece to the control module they often become tangled with one another, making manipulation of the handpiece more difficult.

Multichannel tubing is well represented in the prior art. U.S. Pat. Nos. 6,287,290, 6,527,761 and 6,709,401 teach and describe methods, systems and kits for lung volume reduction which utilize catheters having multiple channels for introduction such expedients as gas for inflating a balloon attached to the catheter, guide channels for the introduction of other catheters and as aspiration channels.

U.S. Pat. No. 6,143,373 teaches and describes a catheter system and method for injection of a liquid embolic composition and a solidification agent for the injection of a liquid and a solidifying agent to close off aneurysm. The multiple lumens are used for the injection of different liquids into the circulatory system.

U.S. Pat. No. 6,066,130 teaches and describes a system for delivering laser energy in which, in one embodiment, a liquid and a guide wire are fed through separate channels in a single catheter.

While these references describe catheter systems having multiple lumens, such systems are designed for insertion into the pulmonary or circulatory systems. None are used for the delivery of irrigating solution to an ophthalmological surgical handpiece while simultaneously providing a path for the aspiration of fluid from the handpiece. None teach or suggest the construction of aspiration/irrigation tubing apparatus connectable to existing handpieces and fluid control consoles as well as to handpieces and consoles specifically designed to accept such apparatus.

The need thus exists for aspiration/irrigation tubing apparatus and connectors that can be connected to existing surgical handpieces and control consoles without modifying them.

A further need exists for such apparatus which allows a surgeon to manipulate the handpiece without kinking the aspiration/irrigation tubing.

Further, a need exists for such tubing and connectors to be made available in inexpensive and disposable versions.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

These and further objects and characteristics of the present invention will become apparent upon consideration of the following drawings, in which.

DETAILED DESCRIPTION OF INVENTION

Figure 1:
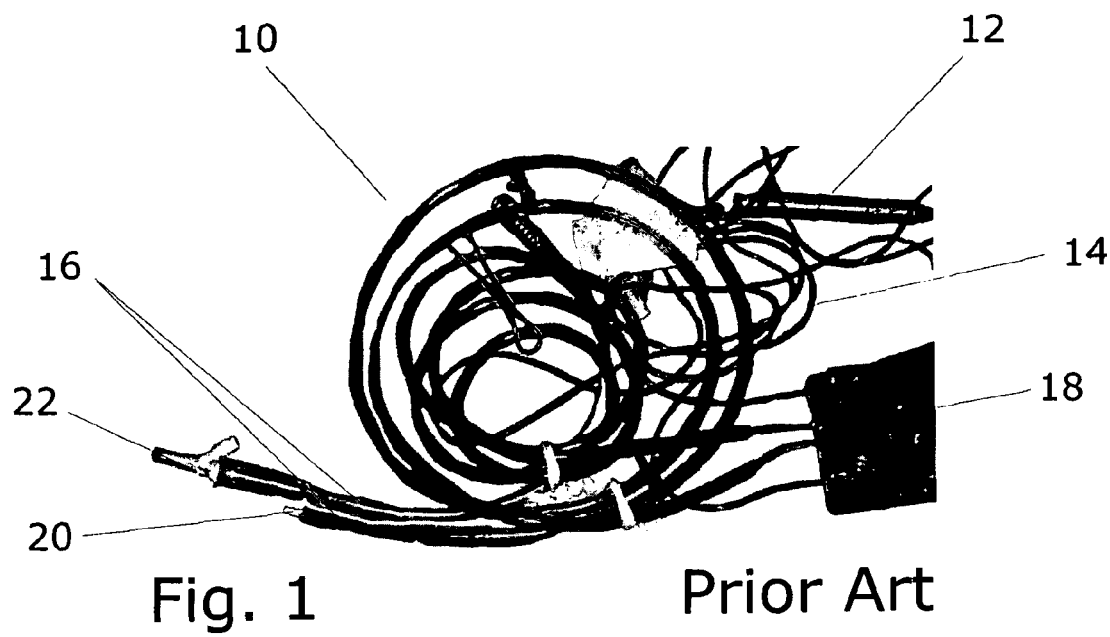
FIG. 1 illustrates a prior art irrigation and aspiration apparatus and its associated tubing.

Referring now to FIG. 1, the numeral 10 indicates generally a prior art phacoemulsification apparatus consisting of a handpiece 12, an irrigation line 14, an aspiration line 16 and a control cassette 18. Control cassette 18 provides a single control apparatus to connect a supply of irrigating to a phacoemulsification handpiece, to complete a path from the handpiece to an aspiration chamber for collecting the aspirated fluid, particles and the like, and an electrical connector for the handpiece.

Figure 2:
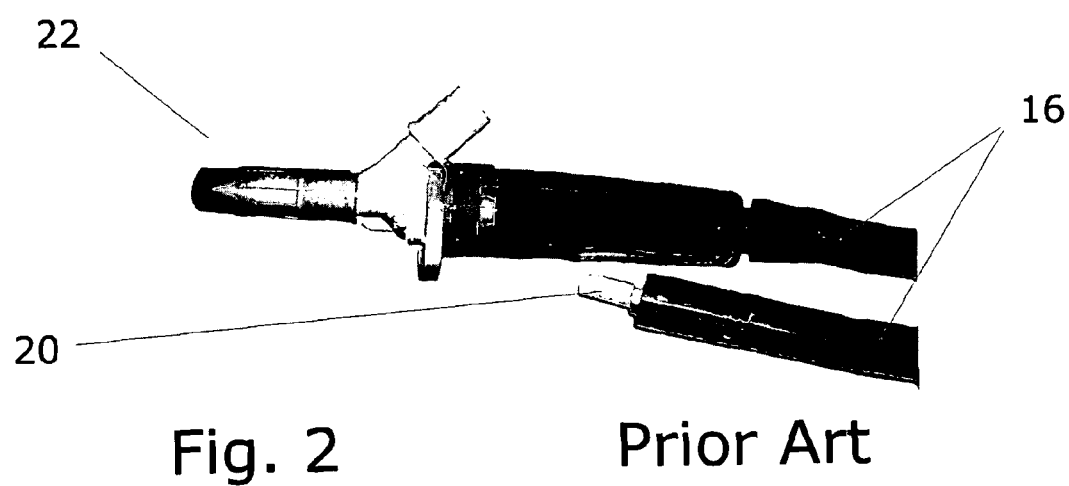
FIG. 2 is an enlarged view of both ends of the irrigation tube of FIG. 1, showing the connectors that secure the tube to the handpiece and the irrigation solution supply bottle.

Referring now to FIG. 2, an enlarged view of prior art irrigation line 14 is shown. Typically, irrigation tube 16 has a male end connector 20 which is inserted into an irrigation connector port on handpiece 12 in a friction fit. FIG. 2 also illustrates a typical irrigation fluid supply connector 22, used to connect line 14 to a container of sterile irrigating solution, such as a flexible plastic bag or the like.

Figure 3:
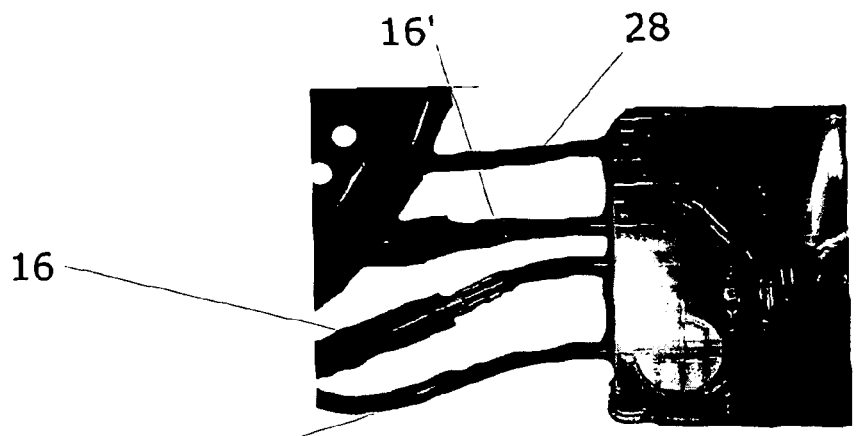
FIG. 3 is an enlarged view of the control module cassette of FIG. 1.

Referring now to FIG. 3, an enlarged view of prior art control cassette 18 is shown demonstrating the connection to cassette 18 of irrigation line 16 (to the handpiece), aspiration line 14 (from the handpiece), irrigation line 16' (from the solution supply container), and an electrical line 28 (which powers the handpiece).

Figure 4:
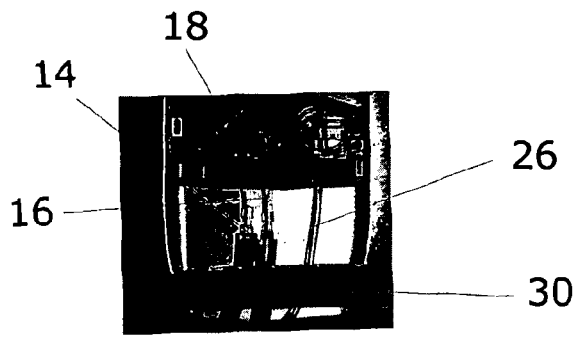
FIG. 4 is an enlarged view of the cassette of FIG. 3 showing the tubing ends taped in place.

Referring now to FIG. 4, lines 26, 14 and 16 are shown attached to prior art cassette 18 with a length of adhesive tape 30 used to secure lines 14, 16 and 26 to cassette 18 in an attempt to keep them from separating from the cassette and/or tangling.

Figure 5:
FIG. 5 illustrates the use of a prior art handpiece with separate irrigation and aspiration tubes attached thereto.

Referring now to FIG. 5, a prior art handpiece 32 is shown being hand held by a surgeon 34 with aspiration line 16 and irrigation line 14 attached. Aspiration line 16 and irrigation line 14 are attached at one end to handpiece 32 and at the other end to control cassette 18. However, in between these attachment points both aspiration line 16 and irrigation line 14 are separate. During surgery, efforts must be made to prevent tubes 14, 16 from kinking and tangling. FIG. 5 shows handpiece 32 as it is held typically during surgery. As can be seen in FIG. 5, lines 14, 16 are separate and must be moved by the surgeon each time the handpiece 32 is moved. Handpiece 32 shown in FIG. 5 is typified by the model 8065 817 801 handpiece sold by Alcon.

In a preferred embodiment of the present invention, a pair of connecting tubes are disposed one within the other to carry out the aspiration and irrigation functions without the snags and tangles experienced when separate tubes are used. As a part of the invention, adaptors are provided to connect the coaxial tubes to existing handpieces.

Figure 6:
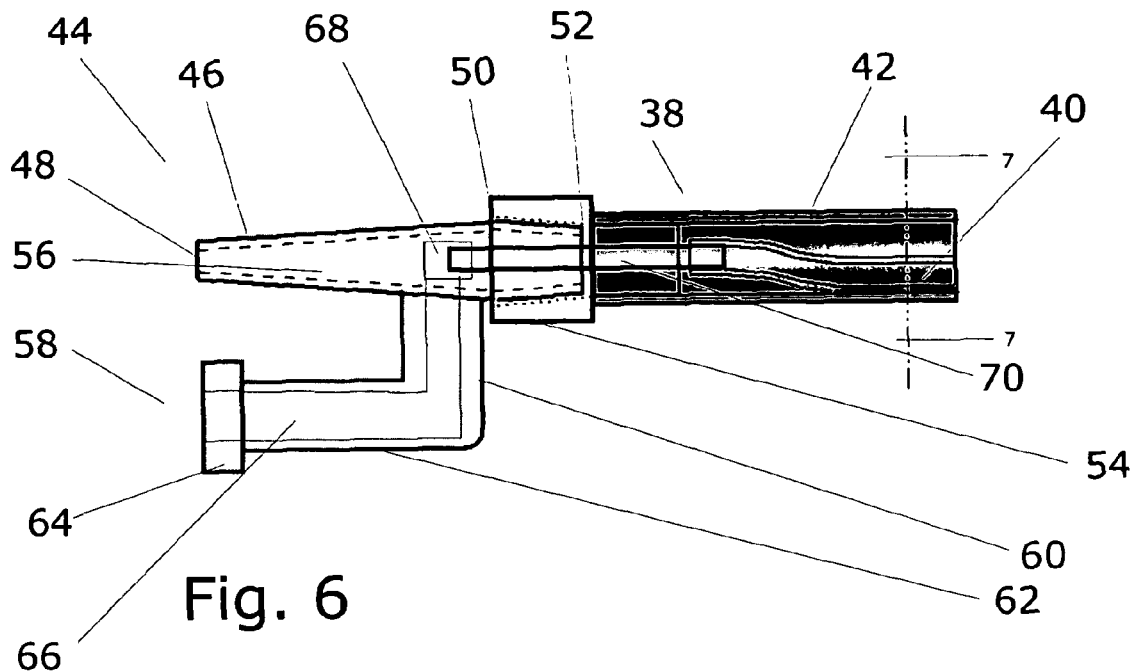
FIG. 6 is an lateral elevational view of an adaptor embodying elements of the present invention.

Referring now to FIG. 6, the numeral 36 identifies a tubing-and-adaptor apparatus constructed in accordance with the present invention. A tubing assembly 38 has an inner tube 40 disposed within an outer tube 42 with both tubes 40 and 42 manufactured from flexible material such as silicone. Tubes 40, 42 will be referred to throughout as "coaxial" even though, strictly speaking, the axes of the tubes are not required to coincide.

Figure 7:
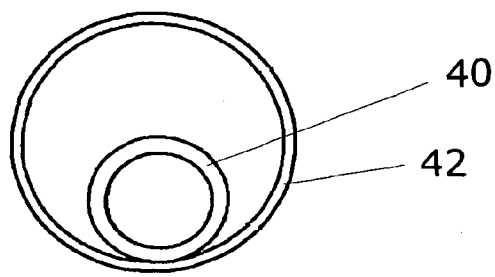
FIG. 7 is a view along line 7-7 of FIG. 6.

Referring to FIG. 7 a cross-section of tubes 40, 42 is shown, illustrating their relative dimensions. Typically a prior art irrigation tube has an inner diameter of about 3.0 mm and an outer diameter of about 5.0 mm, while a typical prior art aspiration tube has an inner diameter of about 1.0 mm and an outer diameter of about 4.0 mm.

In a preferred embodiment of the present invention, aspiration tube 40 has the same inner and outer diameters as the prior art tube and thus has a cross-sectional area of about 7.1 mm$^2$ available for fluid flow. Irrigation tube 42 has an inner diameter of about 7.0 mm and an outer diameter of about 9.0 mm, and a cross-sectional area of about 38.5 mm$^2$. When aspiration tube 40 is placed within irrigation tube 42 and the cross-sectional area measured by the inner diameter of irrigation tube 42 is subtracted from the cross-sectional area measured by the outer diameter of aspiration tube 40 there is a cross-sectional area of about 25.9 mm$^2$ available for irrigation flow, or 18.8 mm$^2$ more than with a conventional irrigation tube. This creates a flow volume 3.6 times greater than that of a prior art irrigation tube, making possible increased irrigation flow while at the same time keeping the irrigation and aspiration tubes from becoming tangled.

FIG. 6 shows tubing assembly 38 attached to an adaptor 44 constructed to allow tubing assembly 38 to be attached to a conventional phacoemulsification handpiece. Adaptor 44 has a first, generally horizontal and tapered hollow plug 46 having a first, open end 48 with plug 46 tapering outwardly from end 48 to a break 50 and, thereafter, tapering inwardly to a second open end 52. Integrally formed with adaptor 44 is a collar 54 within which second end 52 is disposed. A plug channel 56 extends through plug 46 from first end 48 to second end 52.

Integral with and depending from plug 46 is a port leg 58 comprising a first, downwardly depending leg segment 60 and a second leg segment 62 extending at substantially a right angle to segment 60 and terminating in a port collar 64. A port channel 66 begins at and extends through port collar 64, segment 62 and segment 60 terminating in a connector block 68. A connector tube 70, fluid-tightly attached to connector block 68 extends through and past collar 54.

As seen in FIG. 6, tube assembly 38 is connected to adaptor 44 in the following manner. Inner tube 40 is fluid tightly fit to connecting tube 70 while outer tube 42 is inserted into collar 54 and is frictionally and fluid tightly attached to tapered portion 52 of plug 46. In this fashion two separate fluid-tight flow paths are created. The first flow path extends from opening 48 and plug 46 through collar 54 and to outer tube 42. The second flow path begins at port collar 64 and extends through channel 66, connecting block 68 and straight connecting tube 70 to inner tube 40. When connected to a suitable handpiece, plug 48 is inserted into the port on the handpiece through which the irrigating solution is directed while port 58 forms an attachment point for a plug on the handpiece through which aspiration occurs.

Figure 8:
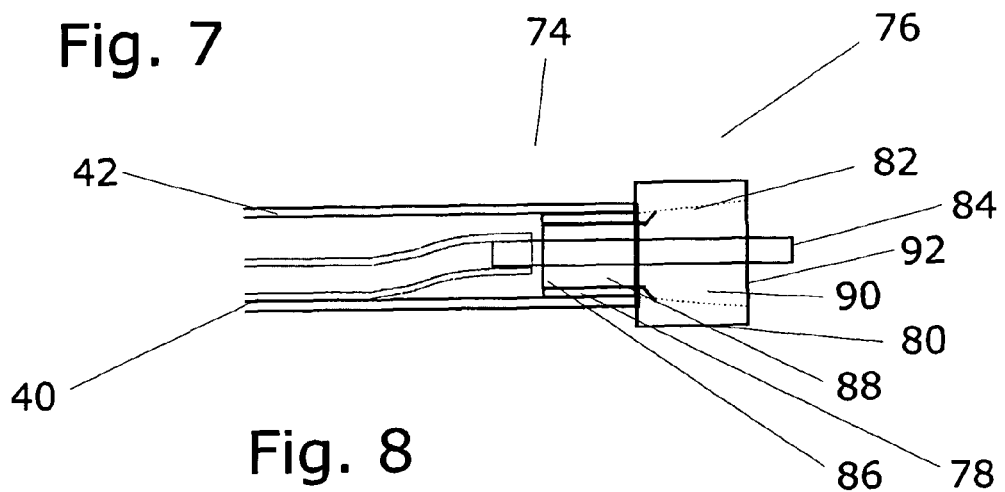
FIG. 8 is a partial sectional view of a second embodiment of an adaptor embodying the present invention.

Referring now to FIG. 8, the numeral 74 identifies a second adaptor or connector having a plug assembly 76 having a first cylindrical section 78 preferably formed as a right cylindrical section and a second or formed integrally with a second plug section 80 larger in diameter than section 78 and having a tapered inner wall 82 formed therewithin.

As seen in FIG. 8, outer tube 42 fits liquid tightly about the outer diameter of first section 78 and abuts against second section 80. Inner tube 40 is attached to a straight tube section 84 which protrudes from plug assembly 76. The configured plug assembly 76 forms a pair of flow channels, the first of which is a relatively large cylindrical flow channel 86 having a first right cylindrical cross section 88 and a second flow section with a frustoconical cross section 90, which tapers outwardly toward an opening 92 through plug section 80. The second flow path is defined by a tube 84 which is inserted, fluid tightly into inner tube 40.

Figure 9:
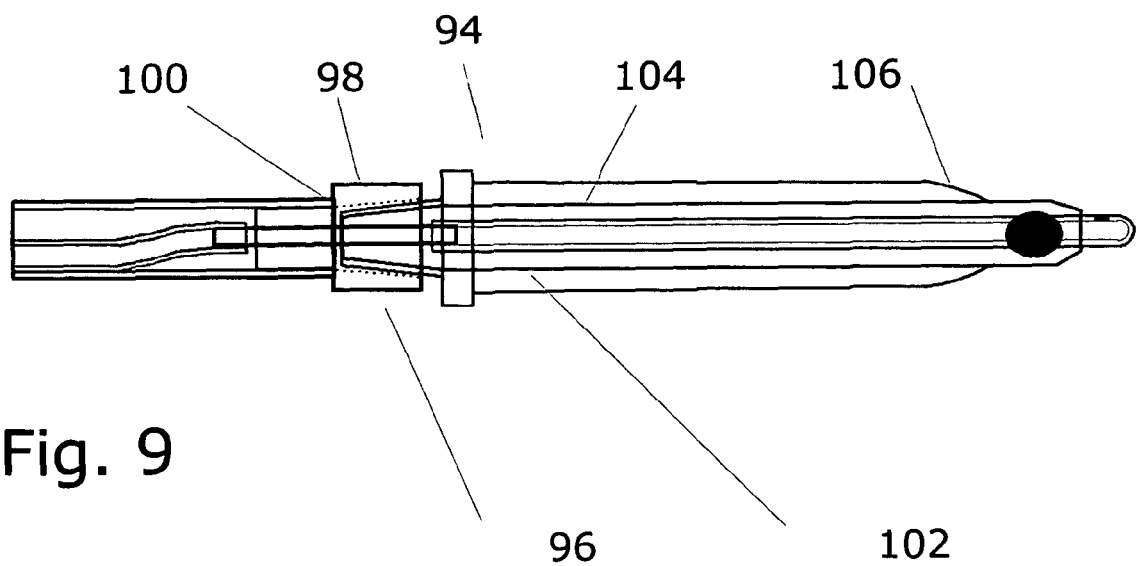
FIG. 9 is a partial sectional view of the adaptor of FIG. 8 attached to a handpiece.

Referring now to FIG. 9, the numeral 94 identifies a handpiece constructed to receive the connector and tube assembly shown in 74. Handpiece 94 has a first end 96 terminating in a hollow nipple 98 tapered outwardly from end 100 to body 102 of handpiece 94. Handpiece 94 also has a central cannula or channel 104 extending from end 96 toward tip 106. As seen in FIG. 9, adaptor and tube assembly 74 is attachable to end piece 94 by inserting the free end of straight tube 84 into cannula 104 while, at the same time, securing plug 86 to tapered end 96 in a fluid-tight fit. Thus, as seen in FIG. 9, a path for aspirating liquids is formed by tip 106, cannula 104, and inner tube 40 while a flow path from infusing liquid is formed by outer tube 42, end 96 and the channel formed through end 96.

I claim:

1. An improved irrigation and aspiration tubing system for use with a phacoemulsification surgical instrument, said system of the type having an irrigating fluid supply source and an aspiration vacuum supply source, said instrument of the type having a first internal flow path for supplying irrigating fluid to a surgical site and a second internal flow path for aspirating fluid and particles from said site, said system comprising:

a first flexible tube segment external of said instrument, having first and second ends, for transporting said irrigating fluid from said irrigating fluid supply to said instrument;

a second flexible tube segment external of said instrument, having first and second ends, forming a path for aspirated fluid and particles from said instrument to said vacuum supply source, said second tube segment positioned wholly within said first tube segment to form first and second lumens, said second lumen comprising said second tube segment;

said first lumen comprising that portion of said first tube segment not occupied by said second tube segment;

means for connecting said first lumen to said second internal flow path;

means for connecting said second lumen to said first internal flow path;

means for connecting said first lumen to said aspiration vacuum supply source; and means for connecting said second lumen to said irrigating fluid supply.

2. The apparatus as set forth in claim 1 wherein said flow path connecting means includes an adaptor enabling attachment of said tubing system to said instrument.

3. The apparatus as recited in claim 1 wherein said first tube segment has an inner diameter sufficiently large to provide a cross-sectional area for fluid flow in excess of about 7 mm$^2$ through said first lumen.

4. The apparatus as recited in claim 1 wherein said first tube segment has an inner diameter of about 7 mm. and said second tube segment has an outer diameter of about 4 mm.

5. The apparatus as recited in claim 1 wherein said first tube segment has an inner diameter sufficiently large to provide a cross-sectional area for fluid flow in excess of about 7 mm$^2$ through said first lumen.

6. The apparatus as recited in claim 1 wherein said first tube segment has an inner diameter of about 7 mm and said second tube segment has an outer diameter of about 4 mm.

7. The apparatus as set forth in claim 1 wherein said first lumen connecting means and said second lumen connecting means together comprise an adaptor enabling attachment of said system to said instrument.

8. The apparatus as recited in claim 7 wherein said adaptor comprises a hollow plug having first and second ends, said first end including a first hollow plug section with a first outside diameter, said first outside diameter being substantially equal to said inside diameter of said first tube segment whereby said first tube segment engages said first plug section in a fluid-tight fit;

a connecting tube having first and second ends, said first connecting tube end having an outside diameter substantially equal to said inside diameter of said second tube segment whereby said first connecting tube end engages said second tube segment in a fluid-tight fit;

said connecting tube extending through said plug;

means for attaching said plug to said first of said instrument flow paths; and means for attaching said connecting means to said second of said instrument flow paths.

9. The apparatus as set forth in claim 1 wherein said first lumen connecting means and said second lumen connecting means together comprise an adaptor enabling attachment of said system to said instrument.

10. The apparatus as recited in claim 1 wherein said irrigating fluid supply source and said aspiration vacuum source comprise a single flow controller, said controller having an irrigating fluid outlet and an aspiration vacuum source inlet;

said first tube segment second end connecting means and said second tube segment second end connecting means comprising together an adaptor, said adaptor configured to allow attachment of said adaptor to said irrigating fluid outlet and said aspiration vacuum source inlet.

11. An improved irrigation and aspiration tubing system for use with a phacoemulsification surgical instrument, said instrument intended to be connected to a source for irrigating fluid and a source for aspiration vacuum, said instrument of the type having a first internal flow path and a second internal flow path, said system comprising:

a first flexible tube segment external of said instrument, having first and second ends, a second flexible tube segment external of said instrument, having first and second ends, said second tube segment positioned wholly within said first tube segment to form first and second lumens, said second lumen comprising said second tube segment;

said first lumen comprising that portion of said first tube segment not occupied by said second tube segment;

means for connecting said first and second lumens to said instrument, said connecting means comprising an adaptor having first and second ends, said first end including a first hollow plug section with a first outside diameter, said first outside diameter being substantially equal to said inside diameter of said first tube segment whereby said first tube segment engages said first plug section in a fluid-tight fit;

a connecting tube having first and second ends, said first connecting tube end having an outside diameter substantially equal to said inside diameter of said second tube segment whereby said first connecting tube end engages said second tube segment in a fluid-tight fit;

said connecting tube extending through said adaptor;

means for attaching said adaptor to said first of said instrument flow paths; and means for attaching said connecting means to said second of said instrument flow paths.

\* \* \* \* \*